United States Patent [19]

Jones

[11] 4,152,869
[45] May 8, 1979

[54] PROPAGATING WOODY PLANT MATERIAL

[75] Inventor: Owen P. Jones, Maidstone, England

[73] Assignees: National Seed Development Organisation Limited, Newton; The Kent Incorporated Society for Promoting Experiments in Horticulture, Maidstone, both of England

[21] Appl. No.: 815,680

[22] Filed: Jul. 14, 1977

[30] Foreign Application Priority Data

Jul. 16, 1976 [GB] United Kingdom ............... 29730/76

[51] Int. Cl.$^2$ ............................................... A01G 1/00
[52] U.S. Cl. ....................................................... 47/58
[58] Field of Search ............................ 47/58, DIG. 3

[56] References Cited

U.S. PATENT DOCUMENTS 3,972,146  8/1976  Boxus ....................................... 47/58

OTHER PUBLICATIONS

Effect of Benzyl Adenine . . . Jones, Nature (London) 1967, 215:1514–1515.
Culture of Malus Tissues . . . Abbott et al., 1976, Scientia Horticulturae, 4:183–189.
Root Imitation in Apple . . . Jones et al., 1976, Journ. Hort. Science, 51:495–499.
Propagation in Vitro, Jones et al., 1977, Journ. Hort. Science, 52:235–238.
Plant Cell, Tissue . . . Reinert et al., 1977, Springer-Verlag, 75, 81, 138, 187, 188 cited.
Propagation of Chrysanthemum . . . Earle et al., J. Amer. Soc. Hort. Sci., 1974, 99(2):128–132.

Primary Examiner—Robert E. Bagwill
Attorney, Agent, or Firm—Oblon, Fisher, Spivak, McClelland & Maier

[57] ABSTRACT

A process of propagating woody plant material of apple, plum or cherry in vitro includes setting a shoot on a nutrient medium including a cytokinin, an auxin and a phenolic compound to produce a number of shoots, excising these shoots and allowing them to multiply again as the same medium any desired number of times, excising individual shoots and rooting these on the same or a similar nutrient medium but from which the cytokinin is omitted and finally growing the resulting plants on.

10 Claims, No Drawings

PROPAGATING WOODY PLANT MATERIAL

This invention relates to the propagating of woody plant material and whilst primarily concerned with apple root stock varieties is also applicable to apple scion varieties and to root stock varieties and scion varieties of plum and cherry.

The invention is applicable generally to the propagation of trees of any variety of these fruits, but is particularly valuable in connection with newly bred varieties. Thus when a new variety of root stock is bred the number of available plants will generally be extremely limited and it may well take five to ten years to produce a sufficient supply to satisfy the market by existing methods. While methods are known for propagating herbaceous plant material in vitro, it has not previously been possible to do this satisfactorily for woody plant material of the fruits referred to above.

According to the present invention a process of propagating woody plant material of apple, plum or cherry in vitro includes setting a shoot on a nutrient medium including a cytokinin, an auxin and a phenolic compound to produce a number of shoots, excising individual shoots and rooting these on the same or a similar nutrient medium but from which the cytokinin is omitted and finally growing the resulting plants on. The proliferation of shoots can be extended indefinitely by subculturing, i.e. by repeating the excision of shoots and culturing on the nutrient medium.

The phenolic compound may be phloridzin or phloroglucinol. Preferably the nutrient medium also includes a gibberellin.

Preferably the auxin is one of the following; ammonium $\beta$-indolyl butyrate (IBA), ammonium $\beta$-indolyl acetate (IAA) or ammonium $\alpha$-napthyl acetate (NAA).

The preferred form of the process in accordance with the invention enables about 15 shoots to be grown in eight weeks from a single shoot and afterwards shoots are multiplied about five fold monthly. In this way it may be possible to obtain more than 100,000 shoots from a single tip within twelve months.

The invention also embraces a plant produced by such a method.

The invention may be put into practice in various ways but one specific embodiment will be briefly described by way of example. The methods employed are as follows, and make use of the following culture medium:

| | MILLIGRAMS PER LITER |
|---|---|
| Thiamine hydrochloride | 0.4 |
| Inositol | 100.0 |
| Gibberellic Acid (GA$_3$) as ammonium salt | 0.1 |
| 6 benzlaminopurine (BAP) | 0.5 or 1.0 |
| Phloroglucinol C$_6$H$_3$(OH)$_3$ . 2H$_2$O | 162.0 |
| Ammonium $\beta$-indolyl butyrate (IBA) | 0.1 |
| FeNaEDTA (Diamino-ethane tetra-acetic acid ferric monosodium salt) | 20.0 |
| Sucrose | 30000.0 |
| Agar | 7000.0 |
| Ammonium nitrate NH$_4$NO$_3$ | 1650.0 |
| Potassium nitrate KNO$_3$ | 1900.0 |
| Calcium Chloride CaCl$_2$ . 2H$_2$O | 440.0 |
| Magnesium Sulphate MgSO$_4$ . 7H$_2$O | 370.0 |
| Potassium Dihydrogen Phosphate KH$_2$PO$_4$ | 170.0 |
| Boric acid H$_3$BO$_3$ | 6.2 |
| Manganese sulphate MnSO$_4$ 4H$_2$O | 22.3 |
| Zinc Sulphate ZnSO$_4$ . 7H$_2$O | 8.6 |
| Potassium iodide KI | 0.83 |
| Sodium molybdate Na$_2$Mo$_4$ . 2H$_2$O | 0.25 |
| Copper Sulphate CuSO$_4$ . 5H$_2$O | 0.025 |
| Cobalt Chloride CoCl$_2$ . 6H$_2$O | 0.025 |

All media constituents were sterilized by autoclaving at 103 KN m$^{-2}$ for 5 min except for IBA and phloroglucinol which were passed through filter (0.45 $\mu$m pore diameter) of the type sold under the Trademark "Millipore".

Aseptic shoot cultures were initiated from shoot tips of 1cm or less of shoots 2 to 5 cm long of M.26 or M.27 apple rootstocks (EMLA virus-free) growing in a greenhouse. All sterile manipulations were carried out in a laminar flow cabinet.

Sterilization

Apple shoots are readily damaged by common surface sterilants but become more resistant after a short period on a culture medium. The following procedure provided undamaged sterile shoot tips: The terminal 2 to 4 cm portions of the shoots were collected into distilled water and then immersed momentarily in 0.01% Mannoxol wetter and immediately afterwards in sodium hypochlorite solution (0.14% w/v available Cl) for 1 min followed by three washes in sterile distilled waer. After the tips has been placed overnight on a culture medium, they were again momentarily immersed in the Mannoxol followed by 40 min in sodium hypochlorite solution (0.84% w/v available Cl) and three washes in sterile distilled water.

Shoot Multiplication

Each tip was planted aseptically in a test-tube with 10ml of the culture medium and after four weeks transferred to a conical flask with 125 mls of the same medium. The tubes were closed with metal caps and flasks with cotton-wool bungs. The cultures were kept at 25° C. with 16 hours light daily from "Crompton" white tubes giving 14 Wm$^{-2}$ at the surface of each culture vessel. After a further five weeks each culture had produced between 20 and 25 shoots.

For producing a large number of shoots the shoot multiplication process described above may be repeated indefinitely before transferring the shoots to a rooting medium as described below.

Root Induction

Shoots were excised from cultures on the phloroglucinol medium and transferred singly to test-tubes, each with 10ml of a medium (which may be termed the rooting medium) which is the same as that described above, but without benzylaminopurine.

Growing on in pots

After six weeks on the rooting medium roots were well developed and plants were placed in 8 cm diameter pots of compost in humid propagating boxes in a shaded greenhouse. After nine days the lids of the boxes were progressively raised over seven days and then the plants removed and grown on naturally in the greenhouse.

Shoot cultures have been multiplied by between 3 and 7 times per month by sub-culturing portions with 2-4 shoots to fresh 125 ml quantities of the medium with phloroglucinol. Some cultures have been maintained sequentially in this way, without any change in proliferation rate for 6 months and during this time approximately 6,000 shoots between 2cm and 5 cm long have been produced which all originated from a single shoot tip inoculum. It should be possible, with a fivefold multiplication rate per month to obtain upwards of 100,000 shoots from one tip in eight months.

It will be appreciated that the invention is not restricted to the details of the specific embodiment described. Thus while particularly valuable for apple root stock it can also be applied to scion varieties and to both root stock and scion varieties of plums and cherries. Moreover, whilst it is preferred to employ a culture including phloridzin or phloroglucinol, phloretic acid, other break-down products of phloridzin, or other phenolic compounds may be employed instead or in addition. Whilst the preferred auxins are IBA, IAA or NAA, other auxins may be included.

What we claim as our invention and desired to secure by Letters Patent is:

1. A process for propagating woody plant material of apple, plum, or cherry in vitro which includes setting a shoot on a nutrient medium including a cytokinin, an auxin and phloridzin to produce a number of shoots, excising individual shoots and rooting these on the same or a similar nutrient medium but from which the cytokinin is omitted, and finally growing the resulting plants on.

2. A process according to claim 1, in which the nutrient medium also includes a gibberellin.

3. A process according to claim 1, in which the auxin comprises at least one of the group consisting of ammonium β-indolyl butyrate, ammonium β-indolyl acetate and ammonium α-naphthyl acetate.

4. A process according to claim 1, in which during the mutliplication stage or the first multiplication stage, the shoot multiplies to produce about fifteen shoots.

5. A process according to claim 1, in which during the multiplication stage or during each subsequent multiplication stage, each individual shoot multiplies to produce about five further shoots.

6. A process for propagating woody plant material of apple, plum, or cherry in vitro which includes setting a shoot on a nutrient medium including a cytokinin, an auxin and phloroglucinol to produce a number of shoots, excising individual shoots and rooting these on the same or a similar nutrient medium but from which the cytokinin is omitted, and finally growing the resulting plants on.

7. A process according to claim 6, in which the nutrient medium also includes gibberellin.

8. A process according to claim 6, in which the auxin comprises at least one of the group consisting of ammonium β-indolyl butyrate, ammonium β-indolyl acetate and ammounium α-naphthyl acetate.

9. A process according to claim 6, in which during the multiplication stage or the first multiplication stage, the shoot multiplies to produce about fifteen shoots.

10. A process according to claim 6, in which during the multiplication stage or during each subsequent multiplication stage, each individual shoot multiplies to produce about five further shoots.

* * * * *